United States Patent [19]

Gliner et al.

[11] Patent Number: 5,749,904
[45] Date of Patent: *May 12, 1998

[54] ELECTROTHERAPY METHOD UTILIZING PATIENT DEPENDENT ELECTRICAL PARAMETERS

[75] Inventors: Bradford E. Gliner, Bellevue; Thomas D. Lyster, Bothell; Clinton S. Cole, Seattle; Daniel J. Powers, Issaquah; Carlton B. Morgan, Bainbridge Island, all of Wash.

[73] Assignee: Heartstream, Inc., Seattle, Wash.

[ * ] Notice: The term of this patent shall not extend beyond the expiration date of Pat. No. 5,601,612.

[21] Appl. No.: 690,529

[22] Filed: Jul. 31, 1996

Related U.S. Application Data

[63] Continuation-in-part of Ser. No. 103,837, Aug. 6, 1993, abandoned, and Ser. No. 227,553, Sep. 14, 1994, Pat. No. 5,607,454.

[51] Int. Cl.$^6$ ..................................................... A61N 1/39
[52] U.S. Cl. .................................................. 607/7; 607/74
[58] Field of Search ........................................ 607/5–7, 74

[56] References Cited

U.S. PATENT DOCUMENTS

| | | |
|---|---|---|
| 3,211,154 | 10/1965 | Becker et al. . |
| 3,241,555 | 3/1966 | Caywood et al. . |
| 3,706,313 | 12/1972 | Milani et al. . |
| 3,782,239 | 1/1974 | Bell . |
| 3,860,009 | 1/1975 | Bell et al. . |
| 3,862,636 | 1/1975 | Bell et al. . |
| 3,886,950 | 6/1975 | Ukkstad et al. . |
| 4,023,573 | 5/1977 | Pantridge et al. . |
| 4,328,808 | 5/1982 | Charbonnier et al. . |
| 4,419,998 | 12/1983 | Heath . |
| 4,473,078 | 9/1984 | Angel . |
| 4,494,552 | 1/1985 | Heath . |

(List continued on next page.)

FOREIGN PATENT DOCUMENTS

| | | |
|---|---|---|
| 0281219 | 9/1988 | European Pat. Off. . |
| 0315368 | 5/1989 | European Pat. Off. . |

(List continued on next page.)

OTHER PUBLICATIONS

Alferness, et al "The influence of shock waveforms on defibrillation efficacy" *IEEE Engineering in Medicine and Biology*, pp. 25–27 (Jun. 1990).

(List continued on next page.)

*Primary Examiner*—William E. Kamm
*Assistant Examiner*—Kennedy J. Schnetzle
*Attorney, Agent, or Firm*—James R. Shay; Cecily Anne Snyder

[57] ABSTRACT

The invention provides a method for delivering electrotherapy to a patient through electrodes connected to a plurality of capacitors, including the steps of discharging at least one of the capacitors across the electrodes to deliver electrical energy to the patient, monitoring a patient-dependent electrical parameter (such as voltage, current or charge) during the discharging step, and adjusting energy delivered to the patient based on a value of the electrical parameter. The adjusting step may include selecting a serial or parallel arrangement for the capacitors based on a value of the electrical parameter.

In another embodiment, the invention provides a method for delivering electrotherapy to a patient through electrodes connectable to a plurality of capacitors including the steps of discharging at least one of the capacitors across the electrodes to deliver electrical energy to the patient in a waveform having at least a first phase and a second phase, monitoring a patient-dependent electrical parameter (such as voltage, current or charge) during the discharging step, and modifying second phase initial voltage based on a value of the electrical parameter. The adjusting step may include selecting a serial or a parallel arrangement for the capacitors based on a value of the electrical parameter.

17 Claims, 10 Drawing Sheets

U.S. PATENT DOCUMENTS

| | | |
|---|---|---|
| 4,504,773 | 3/1985 | Suzuki et al. |
| 4,574,810 | 3/1986 | Lerman |
| 4,595,009 | 6/1986 | Leinders |
| 4,610,254 | 9/1986 | Morgan et al. |
| 4,619,265 | 10/1986 | Morgan et al. |
| 4,637,397 | 1/1987 | Jones et al. |
| 4,745,923 | 5/1988 | Winstrom |
| 4,800,883 | 1/1989 | Winstrom |
| 4,821,723 | 4/1989 | Baker, Jr. et al. |
| 4,840,177 | 6/1989 | Charbonnier et al. |
| 4,848,345 | 7/1989 | Zenkich |
| 4,850,357 | 7/1989 | Bach, Jr. |
| 4,953,551 | 9/1990 | Mehra et al. |
| 4,998,531 | 3/1991 | Bocchi et al. |
| 5,078,134 | 1/1992 | Heilman et al. |
| 5,083,562 | 1/1992 | de Coriolis et al. |
| 5,097,833 | 3/1992 | Campos |
| 5,107,834 | 4/1992 | Ideker et al. |
| 5,111,813 | 5/1992 | Charbonnier et al. |
| 5,111,816 | 5/1992 | Pless et al. |
| 5,199,429 | 4/1993 | Kroll et al. |
| 5,207,219 | 5/1993 | Adams et al. |
| 5,215,081 | 6/1993 | Ostroff |
| 5,222,480 | 6/1993 | Couche et al. |
| 5,222,492 | 6/1993 | Morgan et al. |
| 5,230,336 | 7/1993 | Fain et al. |
| 5,237,989 | 8/1993 | Morgan et al. |
| 5,249,573 | 10/1993 | Fincke et al. |
| 5,275,157 | 1/1994 | Morgan et al. |
| 5,306,291 | 4/1994 | Kroll et al. |
| 5,334,219 | 8/1994 | Kroll |
| 5,334,430 | 8/1994 | Berg et al. |
| 5,352,239 | 10/1994 | Pless |
| 5,370,664 | 12/1994 | Morgan et al. |
| 5,372,606 | 12/1994 | Lang et al. |
| 5,385,575 | 1/1995 | Adams |
| 5,411,525 | 5/1995 | Swanson et al. |
| 5,411,526 | 5/1995 | Kroll et al. |
| 5,431,686 | 7/1995 | Kroll et al. |
| 5,489,293 | 2/1996 | Pless et al. |

FOREIGN PATENT DOCUMENTS

| | | |
|---|---|---|
| 0353341 | 2/1990 | European Pat. Off. |
| 0437104 | 7/1991 | European Pat. Off. |
| 0491649 A | 6/1992 | European Pat. Off. |
| 0507504 | 10/1992 | European Pat. Off. |
| 2070435 | 9/1981 | United Kingdom |
| 2083363 | 3/1982 | United Kingdom |
| 93/16759 | 9/1993 | WIPO |
| 94/21327 | 9/1994 | WIPO |
| 94/22530 | 10/1994 | WIPO |

OTHER PUBLICATIONS

Anderson et al. "The efficacy of trapezoidal wave forms for ventricular defibrillation" *Chest* 70(2):298–300 (1976).

Blilie et al. "Predicting and validating cardiothoracic current flow using finite element modeling" *PACE* 15:563, Abstract 219 (Apr. 1992).

Chapman et al. "Non–thoracotomy internal defibrillation: Improved efficacy with biphasic shocks" *Circulation* 76:312, Abstract No. 1239 (1987).

Cooper et al. "Temporal separation of the two pulses of single capacitor biphasic and dual monophasic waveforms" *Circulation* 84(4):612: Abstract No. 2433 (1991).

Cooper et al. "The effect of phase separation on biphasic waveform defibrillation" *PACE* 16:471–482 (Mar. 1993).

Cooper et al. "The effect of temporal separation of phases on biphasic waveform defibrillation efficacy" *The Annual International Conference of the IEEE Engineering in Medicine and Biology* 13(2):0766–0767 (1991).

Crampton et al. "Low energy ventricular defibrillation and miniature defibrillators" *JAMA* 235(21):2284 (1976).

Dahlback et al. "Ventricular defibrillation with square waves" *The Lancet* (Jul. 2, 1966).

Echt et al. "Biphasic waveform is more efficacious than monophasic waveform for transthoracic cardioversion" *PACE* 16:914, Abstract No. 256 (Apr. 1993).

Feeser et al. "Strength–duration and probability of success curves for defibrillation with biphasic waveforms" *Circulation* 82(6):2128–2141 (1990).

Guse et al. "Defibrillation with low voltage using a left ventricular catheter and four cutaneous patch electrodes in dogs" *PACE* 14:443–451 (Mar. 1991).

Jones et al. "Decreased defibrillator–induced dysfunction with biphasic rectangular waveforms" *Am. J. Physiol.* 247:H792–796 (1984).

Jones et al. "Defibrillator waveshape optimization" *Devices and Tech Meeting* NIH (1982).

Jones et al. "Improved defibrillator waveform safety factor with biphasic waveforms" *Am. J. Physiol.* 245:H60–65 (1983).

Jones et al. "Reduced excitation threshold in potassium depolarized myocardial cells with symmetrical biphasic waveforms" *J. Mol. Cell. Cardiol.* 17(39):XXVII, Abstract No. 39 (1985).

Jude et al. "Fundamentals of cardiopulmonary resuscitation" F.A. Davis & Company, Philadelphia, PA, pp. 98–104 (1965).

Kerber et al. "Energy, current and success in defibrillation and cardioversion: clinical studies using an automated impedance–based method of energy adjustment" *Circulation* 77(5):1038 (May 1988).

Knickerbocker et al. "A portable defibrillator" *IEEE Trans on Power and Apparatus Systems* 69:1089–1093 (1963).

Kuowenhoven "The development of the defibrillator" *Annals of Internal Medicine* 71(3):449–458 (1969).

Langer et al. "Considerations in the development of the automatic implantable defibrillator" *Medical Instrumentation* 10(3):163–167 (1976).

Lerman et al. "Current–based versus energy–based ventricular defibrillation: A prospective study" *JACC* 12(5):1259–1264 (1988).

Lindsay et al. "Prospective evaluation of a sequential pacing and high energy bi–directional shock algorithm for transvenous cardioversion in patients with ventricular tachycardia" *Circulation* 76(3):601–609 (1987).

Mirowski et al. "Clinical treatment of life threatening ventricular tachyarrhythmias with the automatic implantable defibrillator" *American Heart J.* 102(2):265–270 (1981).

Mirowski et al. "Temination of malignant ventricular arrhythmias with an implanted automatic defibrillator in human beings" *New Engl J. Med.* 303(6):322–324 (1980).

Podolsky "Keeping the beat alive" *U.S. News & World Report* (Jul. 22, 1991).

Product Brochure First Medic Semi–Automatic Defibrillators (1994), Spacelabs Medical Products, 15220 N.E. 40th Street, P.O. Box 97013, Redmond, Washington.

Product Brochure for the Shock Advisory System (1987), Physio–Control, 11811 Willow Road Northeast, P.O. Box 97006, Redmond WA 98073.9706.

Product information for Model H MSA Portable Defibrillator (Bulletin No. 1108-2).

Product information for MSA Portable Defibrillator (Bulletin No. 1108-1).

Redd (editor), "Defibrillation with biphasic waveform may increase safety, improve survival" *Medlines* pp. 1-2 (Jun.-Jul. 1984).

Saksena et al. "A prospective evaluation of single and dual current pathways for transvenous cardioversion in rapid ventricular tachycardia" *PACE* 10:1130-1141 (Sep.-Oct. 1987).

Saksena et al. "Development for future implantable cardioverters and defibrillators" *PACE* 10:1342-1358 (Nov.-Dec. 1987).

Schuder "The role of an engineering oriented medical research group in developing improved methods and devices for achieving venticular defibrillator: The University of Missouri experience" *PACE* 16:95-124 (Jan. 1993).

Schuder et al. "A multielectrode-time sequential laboratory defibrillator for the study of implanted electrode systems" *Amer. Soc. Artif. Int. Organs* XVIII:514-519 (1972).

Schuder et al. "Comparison of effectiveness of relay-switched, one-cycle quasisinusoidal waveform with critically damped sinusoid waveform in transthoracic defibrillation of 100-kilogram calves" *Medical Instrumentation* 22(6):281-285.

Schuder et al. "Defibrillation of 100 kg calves with asymmetrical, bi-directional, rectangular pulses" *Card. Res.* 18:419-426 (1984).

Schuder et al. "Development of automatic implanted defibrillator" *Devices & Tech Meeting* NIH (1981).

Schuder et al. "One-cycle bidirectional rectangular wave shocks for open chest defibrillation in the calf" *Abs. Am. Soc. Artif. Intern. Organs* 9:16.

Schuder et al. "Transthoracic ventricular defibrillation in the 100 kg calf with symmetrical one-cycle bidirectional rectangular wave stimuli" *IEEE Trans. BME* 30(7):415-422 (1983).

Schuder et al. "Transthoracic ventricular defibrillation with Square-wave stimuli; one-half cycle" *Cir. Res.* XV:258-264 (1964).

Schuder et al. "Ultrahigh-energy hydrogen thyratron/SCR bidirectional waveform defibrillator" *Med. & Bio. Eng. & Comput.* 20:419-424 (1982).

Schuder et al. "Waveform dependency in defibrillating 100 kg calves" *Devices & Tech. Meeting* NIH (1981).

Schuder et al. "Waveform dependency in defibrillating 100 kg calves" *Devices & Tech Meeting NIH* (1982).

Schuder et al. "Waveform dependency in defibrillation" *Devices & Tech Meeting NIH* (1981).

Stanton et al. "Relationship between defibrillation threshold and upper limit of vulnerablilty in humans" *PACE* 15:563, Abstract 221 (Apr. 1992).

Tang et al. "Strength duration curve for ventricular defibrillation using biphasic waveforms" *PACE*, 10: Abstract No. 49 (1987).

Tang et al. "Ventricular defibrillation using biphasic waveforms of different phasic duration" *PACE* 10:Abstract No. 47 (1987).

Tang et al. "Ventricular defibrillation using biphasic waveforms: The importance of phasic duration" *JACC* 13(1):207-214 (1989).

Walcott et al. "Comparison of monophasic, biphasic, and the edmark waveform for external defibrillation" *PACE* 15:563, Abstract 218 (Apr. 1992).

Wathen et al. "Improved defibrillation efficacy using four nonthoracotomy leads for sequential pulse defibrillation" *PACE* 15:563, Abstract 220 (Apr. 1992).

Wetherbee et al. "Subcutaneous patch electrode—A means to obviate thoracotomy for implantation of the automatic cardioverter defibrillation system?" *Circ.* 72:384, Abstract No. 1536 (1985).

Winkle et al. "The implantable defibrillator in ventricular arrhythmias" *Hospital Practice*, pp. 149-165 (Mar. 1983).

Winkle et al., "Improved low energy defibrillation efficacy in man using a biphasic truncated exponential waveform" *JACC* 9(2):142A (1987).

Zipes "Sudden cardiac death" *Circulation* 85(1):160-166 (1992).

5,749,904

ELECTROTHERAPY METHOD UTILIZING PATIENT DEPENDENT ELECTRICAL PARAMETERS

This application is a continuation-in-part of U.S. patent application Ser. No. 08/103,837, "Electrotherapy Method and Apparatus," filed Aug. 6, 1993, now abandoned, and a continuation-in-part of U.S. patent appilication Ser. No. 08/227,553, "Electrotherapy Method and Apparatus," filed Apr. 14, 1994, now U.S. Pat. No. 5,607,454, the disclosures of which are incorporated herein by reference.

BACKGROUND OF THE INVENTION

This invention relates generally to an electrotherapy method and apparatus for delivering a shock to a patient's heart. In particular, this invention relates to a method and apparatus for shaping the electrical waveform delivered by an external defibrillator based on an electrical parameter measured during delivery of the waveform.

Sudden cardiac death is the leading cause of death in the United States. Most sudden cardiac death is caused by ventricular fibrillation, in which the heart's muscle fibers contract without coordination, thereby interrupting normal blood flow to the body. The only effective treatment for ventricular fibrillation is electrical defibrillation, which applies an electrical shock to the patient's heart.

To be effective, the defibrillation shock must be delivered to the patient within minutes of the onset of ventricular fibrillation. Studies have shown that defibrillation shocks delivered within one minute after ventricular fibrillation begins achieve up to 100% survival rate. The survival rate falls to approximately 30% if 6 minutes elapse before the shock is administered. Beyond 12 minutes, the survival rate approaches zero.

One way of delivering rapid defibrillation shocks is through the use of implantable defibrillators. Implantable defibrillators are surgically implanted in patients who have a high likelihood of needing electrotherapy in the future. Implanted defibrillators typically monitor the patient's heart activity and automatically supply electrotherapeutic pulses directly to the patient's heart when indicated. Thus, implanted defibrillators permit the patient to function in a somewhat normal fashion away from the watchful eye of medical personnel. Implantable defibrillators are expensive, however, and are used on only a small fraction of the total population at risk for sudden cardiac death.

External defibrillators send electrical pulses to the patient's heart through electrodes applied to the patient's torso. External defibrillators are useful in the emergency room, the operating room, emergency medical vehicles or other situations where there may be an unanticipated need to provide electrotherapy to a patient on short notice. The advantage of external defibrillators is that they may be used on a patient as needed, then subsequently moved to be used with another patient.

However, because external defibrillators deliver their electrotherapeutic pulses to the patient's heart indirectly (ie., from the surface of the patients skin rather than directly to the heart), they must operate at higher energies, voltages and/or currents than implanted defibrillators. These high energy, voltage and current requirements have made existing external defibrillators large, heavy and expensive, particularly due to the large size of the capacitors or other energy storage media required by these prior art devices. The size and weight of prior art external defibrillators have limited their utility for rapid response by emergency medical response teams.

Defibrillator waveforms, ie., time plots of the delivered current or voltage pulses, are characterized according to the shape, polarity, duration and number of pulse phases. Most current external defibrillators deliver monophasic current or voltage electrotherapeutic pulses, although some deliver biphasic sinusoidal pulses. Some prior art implantable defibrillators, on the other hand, use truncated exponential, biphasic waveforms. Examples of biphasic implantable defibrillators may be found in U.S. Pat. No. 4,821,723 to Baker, Jr., et al.; U.S. Pat. No. 5,083,562 to de Coriolis et al.; U.S. Pat. No. 4,800,883 to Winstrom; U.S. Pat. No. 4,850,357 to Bach, Jr.; U.S. Pat. No. 4,953,551 to Mehra et al.; and U.S. Pat. No. 5,230,336 to Fain et al.

Because each implanted defibrillator is dedicated to a single patient, its operating parameters, such as electrical pulse amplitudes and total energy delivered, may be effectively titrated to the physiology of the patient to optimize the defibrillator's effectiveness. Thus, for example, the initial voltage, first phase duration and total pulse duration may be set when the device is implanted to deliver the desired amount of energy or to achieve a desired start and end voltage differential (i.e., a constant tilt). Even when an implanted defibrillator has the ability to change its operating parameters to compensate for changes in the impedance of the defibrillators leads and/or the patient's heart (as discussed in the Fain patent), the range of potential impedance changes for a single implantation in a single patient is relatively small.

In contrast, because external defibrillator electrodes are not in direct contact with the patient's heart, and because external defibrillators must be able to be used on a variety of patients having a variety of physiological differences, external defibrillators must operate according to pulse amplitude and duration parameters that will be effective in most patients, no matter what the patient's physiology. For example, the impedance presented by the tissue between external defibrillator electrodes and the patient's heart varies from patient to patient, thereby varying the intensity and waveform shape of the shock actually delivered to the patient's heart for a given initial pulse amplitude and duration. Pulse amplitudes and durations effective to treat low impedance patients do not necessarily deliver effective and energy efficient treatments to high impedance patients.

External defibrillators may be subjected to extreme load conditions which could potentially damage the waveform generator circuits. For example, improperly applied defibrillator electrodes may create a very low impedance current path during the shock delivery, which could result in excessively high current within the waveform circuit. Thus, an external defibrillator has an additional design requirement to limit the peak current to safe levels in the waveform circuit, which is not normally a concern for implanted defibrillators.

Prior art defibrillators have not fully addressed the patient variability problem. One prior art approach to this problem was to provide an external defibrillator with multiple energy settings that could be selected by the user. A common protocol for using such a defibrillator was to attempt defibrillation at an initial energy setting suitable for defibrillating a patient of average impedance, then raise the energy setting for subsequent defibrillation attempts in the event that the initial setting failed. The repeated defibrillation attempts require additional energy and add to patient risk.

Some prior art defibrillators measure the patient impedance, or a parameter related to patient impedance and alter the shape of a subsequent defibrillation shock based on the earlier measurement. For example, the implanted defibrillator described in the Fain patent delivers a defibrillation shock of predetermined shape to the patient's heart in response to a detected arrhythmia. The Fain device measures the system impedance during delivery of that shock and uses the measured impedance to alter the shape of a subsequently delivered shock.

Another example of the measurement and use of patient impedance information in prior art defibrillators is described in an article written by R. E. Kerber, et al., "Energy, current, and success in defibrillation and cardioversion," Circulation (May 1988). The authors describe an external defibrillator that administers a test pulse to the patient prior to administering the defibrillation shock. The test pulse is used to measure patient impedance; the defibrillator adjusts the amount of energy delivered by the shock in response to the measured patient impedance. The shape of the delivered waveform is a damped sinusoid.

SUMMARY OF THE INVENTION

This invention provides an external defibrillator and defibrillation method that automatically compensates for patient-to-patient impedance differences in the delivery of electrotherapeutic pulses for defibrillation and cardioversion. In a preferred embodiment, the defibrillator has an energy source that may be discharged through electrodes on the patient to provide a biphasic voltage or current pulse. In one aspect of the invention, the first and second phase duration and initial first phase amplitude are predetermined values. In a second aspect of the invention, the duration of the first phase of the pulse may be extended if the amplitude of the first phase of the pulse fails to fall to a threshold value by the end of the predetermined first phase duration, as might occur with a high impedance patient. In a third aspect of the invention, the first phase ends when the first phase amplitude drops below a threshold value or when the first phase duration reaches a threshold time value, whichever comes first, as might occur with a low to average impedance patient.

In yet another embodiment, the invention provides a method for delivering electrotherapy to a patient through electrodes connected to a plurality of capacitors, including the steps of discharging at least one of the capacitors across the electrodes to deliver electrical energy to the patient, monitoring a patient-dependent electrical parameter (such as voltage, current or charge) during the discharging step, and adjusting energy delivered to the patient based on a value of the electrical parameter. The adjusting step may include selecting a serial or parallel arrangement for the capacitors based on a value of the electrical parameter.

In another embodiment, the invention provides a method for delivering electrotherapy to a patient through electrodes connectable to a plurality of capacitors including the steps of discharging at least one of the capacitors across the electrodes to deliver electrical energy to the patient in a waveform having at least a first phase and a second phase, monitoring a patient-dependent electrical parameter (such as voltage, current or charge) during the discharging step, and modifying second phase initial voltage based on a value of the electrical parameter. The adjusting step may include selecting a serial or a parallel arrangement for the capacitors based on a value of the electrical parameter.

The invention is described in more detail below with reference to the drawings.

DETAILED DESCRIPTION OF THE PREFERRED EMBODIMENT

Figure 1:
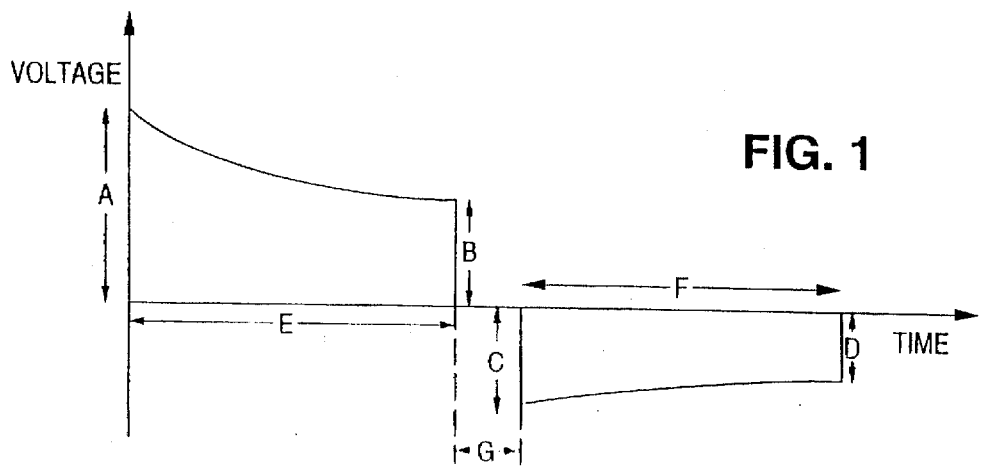
FIG. 1 is a schematic representation of a low-tilt biphasic electrotherapeutic waveform according to a first aspect of this invention.
Figure 2:
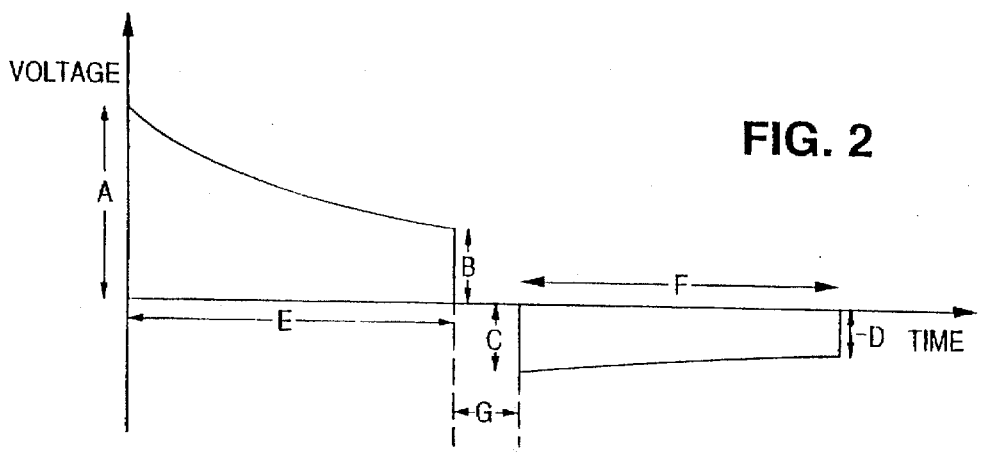
FIG. 2 is a schematic representation of a high-tilt biphasic electrotherapeutic waveform according to the first aspect of this invention.

FIGS. 1 and 2 illustrate the patient-to-patient differences that an external defibrillator design must take into account. These figures are schematic representations of truncated exponential biphasic waveforms delivered to two different patients from an external defibrillator according to the electrotherapy method of this invention for defibrillation or cardioversion. In these drawings, the vertical axis is voltage, and the horizontal axis is time. The principles discussed here are applicable to waveforms described in terms of current versus time as well, however.

The waveform shown in FIG. 1 is called a low-tilt waveform, and the waveform shown in FIG. 2 is called a high-tilt waveform, where tilt H is defined as a percent as follows:

$$H = \frac{|A| - |D|}{|A|} \times 100$$

As shown in FIGS. 1 and 2, A is the initial first phase voltage and D is the second phase terminal voltage. The first phase terminal voltage B results from the exponential decay over time of the initial voltage A through the patient, and the second phase terminal voltage D results from the exponential decay of the second phase initial voltage C in the same manner. The starting voltages and first and second phase durations of the FIG. 1 and FIG. 2 waveforms are the same; the differences in end voltages B and D reflect differences in patient impedance.

Prior art disclosures of the use of truncated exponential biphasic waveforms in implantable defibrillators have provided little guidance for the design of an external defibrillator that will achieve acceptable defibrillation or cardioversion rates across a wide population of patients. The defibrillator operating voltages and energy delivery requirements affect the size, cost, weight and availability of components. In particular, operating voltage requirements affect the choice of switch and capacitor technologies. Total energy delivery requirements affect defibrillator battery and capacitor choices. We have determined that, for a given patient, externally-applied truncated exponential biphasic waveforms defibrillate at lower voltages and at lower total delivered energies than externally-applied monophasic waveforms. In addition, we have determined that there is a complex relationship between total pulse duration, first to second phase duration ratio, initial voltage, total energy and total tilt.

Up to a point, the more energy delivered to a patient in an electrotherapeutic pulse, the more likely the defibrillation attempt will succeed. Low-tilt biphasic waveforms achieve effective defibrillation rates with less delivered energy than high-tilt waveforms. However, low-tilt waveforms are energy inefficient, since much of the stored energy is not delivered to the patient. On the other hand, defibrillators delivering high-tilt biphasic waveforms deliver more of the stored energy to the patient than defibrillators delivering low-tilt waveforms while maintaining high efficacy up to a certain critical tilt value. Thus, for a given capacitor, a given initial voltage and fixed phase durations, high impedance patients receive a waveform with less total energy and lower peak currents but better conversion properties per unit of energy delivered, and low impedance patients receive a waveform with more delivered energy and higher peak currents. There appears to be an optimum tilt range in which high and low impedance patients will receive effective and efficient therapy. An optimum capacitor charged to a predetermined voltage can be chosen to deliver an effective and efficient waveform across a population of patients having a variety of physiological differences.

This invention is a defibrillator and defibrillation method that takes advantage of this relationship between waveform tilt and total energy delivered in high and low impedance patients. In one aspect of the invention, the defibrillator operates in an open loop, i.e., without any feedback regarding patient impedance parameters and with preset pulse phase durations. The preset parameters of the waveforms shown in FIG. 1 and 2 are therefore the initial voltage A of the first phase of the pulse, the duration E of the first phase, the interphase duration G, and the duration F of the second phase. The terminal voltage B of the first phase, the initial voltage C of the second phase, and the terminal voltage D of the second phase are dependent upon the physiological parameters of the patient and the physical connection between the electrodes and the patient.

For example, if the patient impedance (ie., the total impedance between the two electrodes) is high, the amount of voltage drop (exponential decay) from the initial voltage A to the terminal voltage B during time E will be lower (FIG. 1) than if the patient impedance is low (FIG. 2). The same is true for the initial and terminal voltages of the second phase during time F. The values of A, E, G and F are set to optimize defibrillation and/or cardioversion efficacy across a population of patients. Thus, high impedance patients receive a low-tilt waveform that is more effective per unit of delivered energy, and low impedance patients receive a high-tilt waveform that delivers more of the stored energy and is therefore more energy efficient.

Figure 4:
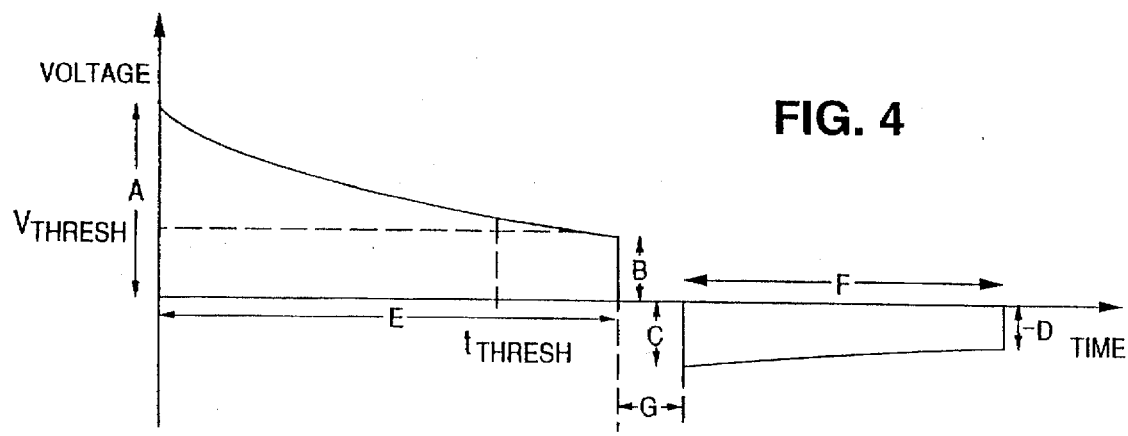
FIG. 4 is a schematic representation of a biphasic waveform delivered according to the second aspect of this invention.
Figure 3:
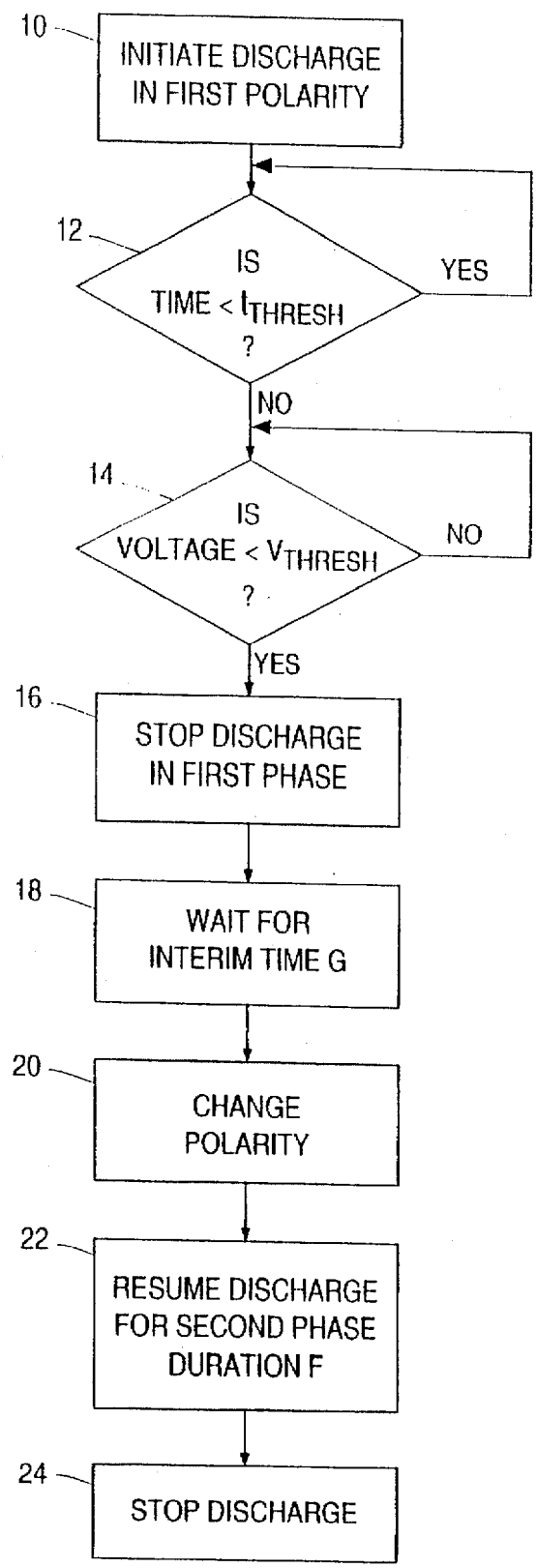
FIG. 3 is a flow chart demonstrating part of an electrotherapy method according to a second aspect of this invention.
Figure 5:
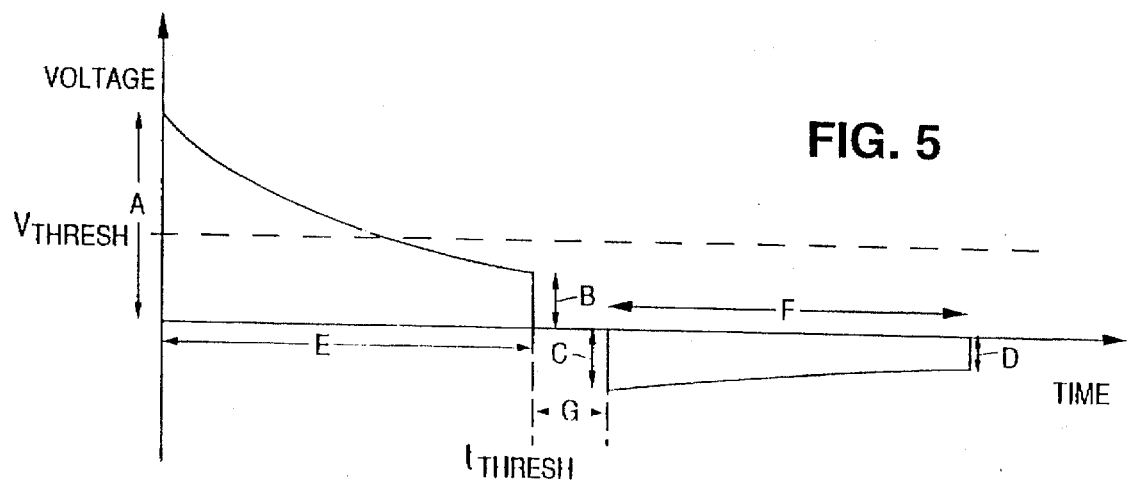
FIG. 5 is a schematic representation of a biphasic waveform delivered according to the second aspect of this invention.

Another feature of biphasic waveforms is that waveforms with relatively longer first phases have better conversion properties than waveforms with equal or shorter first phases, provided the total duration exceeds a critical minimum. Therefore, in the case of high impedance patients, it may be desirable to extend the first phase of the biphasic waveform (while the second phase duration is kept constant) to increase the overall efficacy of the electrotherapy by delivering a more efficacious waveform and to increase the total amount of energy delivered. FIGS. 3–5 demonstrate a defibrillation method according to this second aspect of the invention in which information related to patient impedance is fed back to the defibrillator to change the parameters of the delivered electrotherapeutic pulse.

FIG. 3 is a flow chart showing the method steps following the decision (by an operator or by the defibrillator itself) to apply an electrotherapeutic shock to the patient through electrodes attached to the patient and charging of the energy source, e.g., the defibrillator's capacitor or capacitor bank, to the initial first phase voltage A. Block 10 represents initiation of the first phase of the pulse in a first polarity. Discharge may be initiated manually by the user or automatically in response to patient heart activity measurements (e.g., ECG signals) received by the defibrillator through the electrodes and analyzed by the defibrillator controller in a manner known in the art.

Discharge of the first phase continues for at least a threshold time $t_{THRESH}$, as shown by block 12 of FIG. 3. If, at the end of time $t_{THRESH}$, the voltage measured across the energy source has not dropped below the minimum first phase terminal voltage threshold $V_{THRESH}$, first phase discharge continues, as shown in block 14 of FIG. 3. For high impedance patients, this situation results in an extension of the first phase duration beyond $V_{THRESH}$, as shown in FIG. 4, until the measured voltage drops below the threshold $V_{THRESH}$. Discharge then ends to complete the first phase, as represented by block 16 of FIG. 3. If, on the other hand, the patient has low impedance, the voltage will have dropped below $V_{THRESH}$ when the time threshold is reached, resulting in a waveform like the one shown in FIG. 5.

At the end of the first phase, and after a predetermined interim period G, the polarity of the energy source connection to the electrodes is switched, as represented by blocks 18 and 20 of FIG. 3. Discharge of the second phase of the biphasic pulse then commences and continues for a predetermined second phase duration F, as represented by block 22 of FIG. 3, then ceases. This compensating electrotherapy method ensures that the energy is delivered by the defibrillator in the most efficacious manner by providing for a minimum waveform tilt and by extending the first phase duration to meet the requirements of a particular patient.

Because this method increases the waveform tilt for high impedance patients and delivers more of the energy from the energy source than a method without compensation, the defibrillator's energy source can be smaller than in prior art external defibrillators, thereby minimizing defibrillator size, weight and expense. It should be noted that the waveforms shown in FIGS. 4 and 5 could be expressed in terms of current versus time using a predetermined current threshold value without departing from the scope of the invention.

Figure 7:
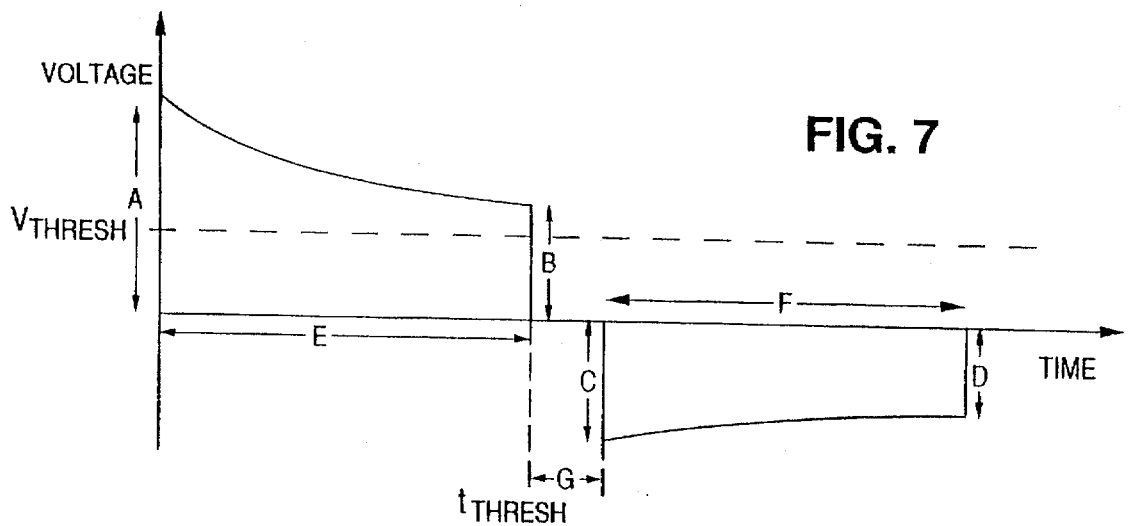
FIG. 7 is a schematic representation of a biphasic waveform delivered according to the third aspect of this invention.
Figure 8:
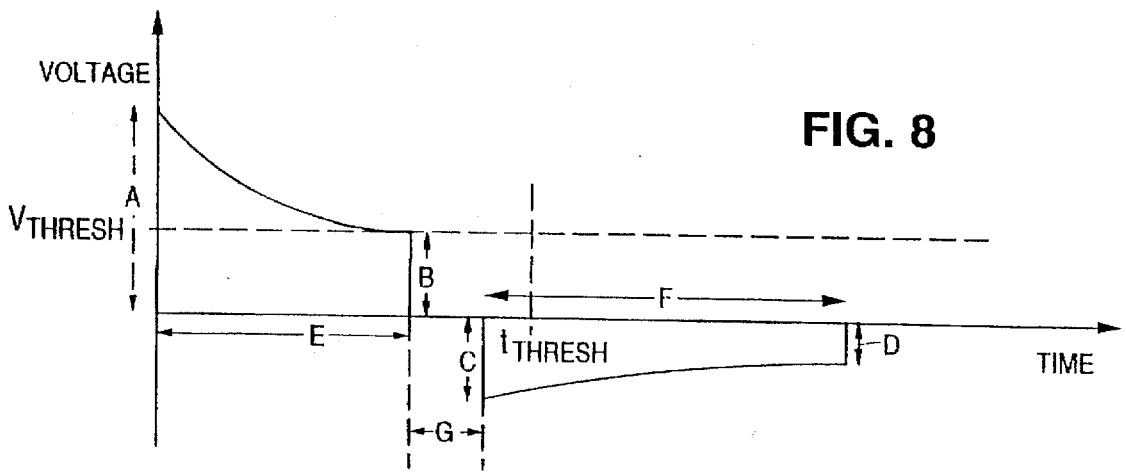
FIG. 8 is a schematic representation of a biphasic waveform delivered according to the third aspect of this invention.
Figure 6:
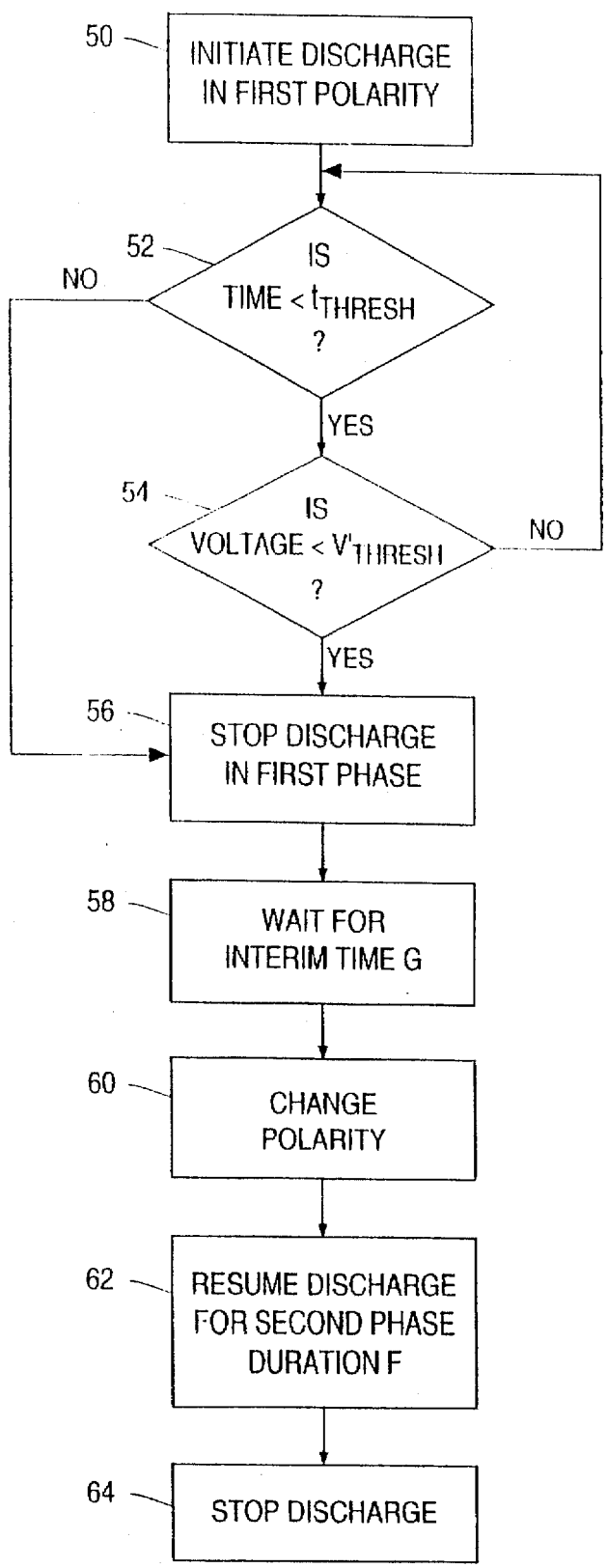
FIG. 6 is a flow chart demonstrating part of an electrotherapy method according to a third aspect of this invention.

FIGS. 6–8 illustrate a third aspect of this invention that prevents the delivered waveform from exceeding a maximum tilt (i.e., maximum delivered energy) in low impedance patients. As shown by blocks 52 and 54 in FIG. 6, the first phase discharge stops either at the end of a predetermined time $t_{THRESH}$ or when the first phase voltage drops below $V'_{THRESH}$. The second phase begins after an interim period G and continues for a preset period F as in the second aspect of the invention. Thus, in high impedance patients, the first phase ends at time $t_{THRESH}$, even if the voltage has not yet fallen below $V'_{THRESH}$, as shown in FIG. 7. In low impedance patients, on the other hand, the first phase of the delivered waveform could be shorter in duration than the time $t_{THRESH}$, as shown in FIG. 8.

Once again, the waveforms shown in FIGS. 7 and 8 could be expressed in terms of current versus time using a predetermined current threshold value without departing from the scope of the invention.

Figure 9:
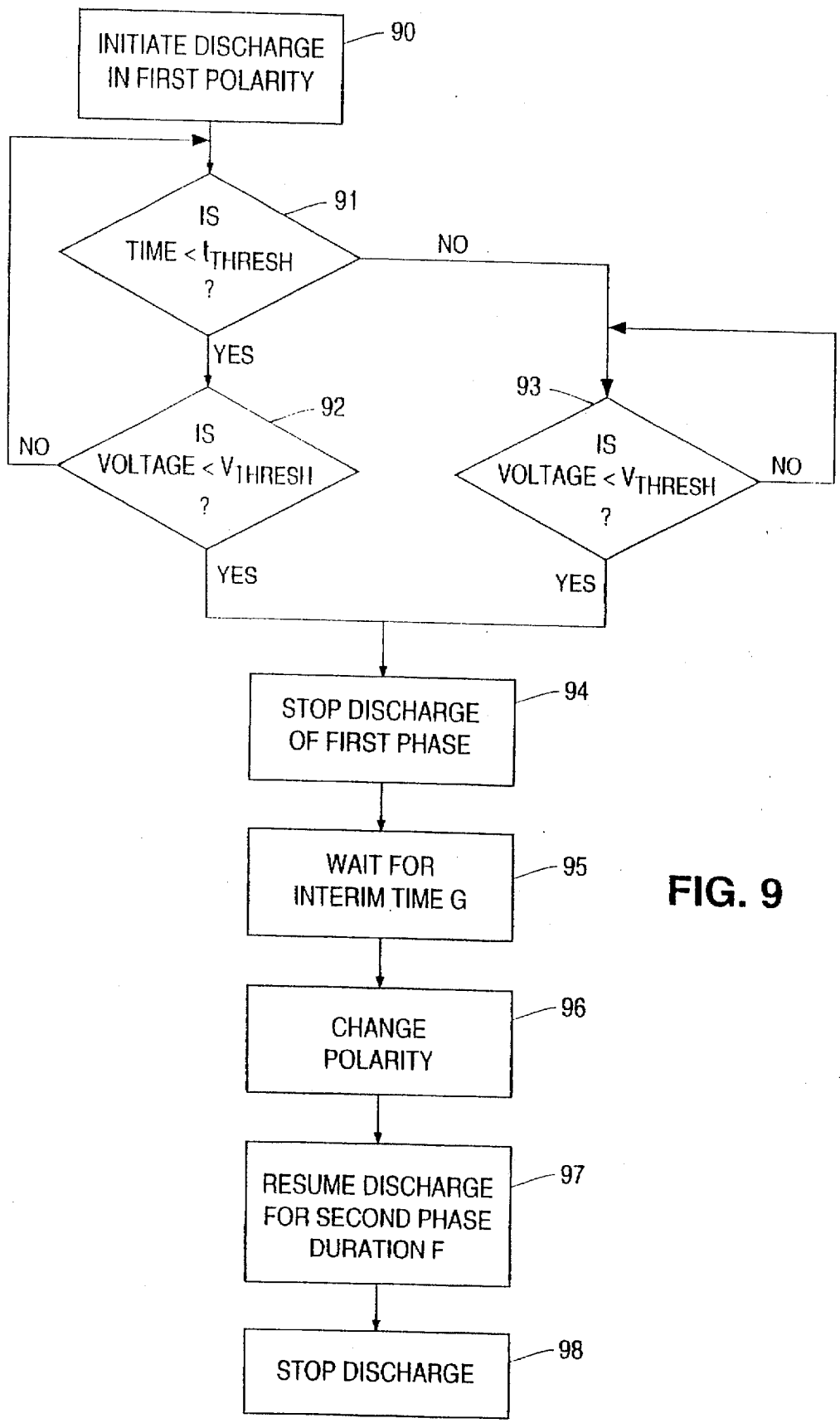
FIG. 9 is a flow chart demonstrating part of an electrotherapy method according to a combination of the second and third aspects of this invention.

FIG. 9 is a flow chart illustrating a combination of the defibrillation methods illustrated in FIGS. 3 and 6. In this combination method, the first phase of the biphasic waveform will end if the voltage reaches a first voltage threshold $V'_{THRESH}$ prior to the first phase duration threshold $T_{THRESH}$, as shown by blocks 91 and 92. This defibrillator decision path delivers a waveform like that shown in FIG. 8 for low impedance patients. For high impedance patients, on the other hand, if at the expiration of $t_{THRESH}$ the voltage has not fallen below $V'_{THRESH}$, the duration of the first phase is extended beyond $t_{THRESH}$ until the voltage measured across the electrodes reaches a second voltage threshold $V_{THRESH}$, as shown in decision blocks 91 and 93. This defibrillator method path will deliver a waveform like that shown in FIG. 4.

In alternative embodiments of this invention, the second phase pulse could be a function of the first phase voltage, current or time instead of having a fixed time duration. In addition, any of the above embodiments could provide for alternating initial polarities in successive monophasic or biphasic pulses. In other words, if in the first biphasic waveform delivered by the system the first phase is a positive voltage or current pulse followed by a second phase negative voltage or current pulse, the second biphasic waveform delivered by the system would be a negative first phase voltage or current pulse followed by a positive second phase voltage or current pulse. This arrangement would minimize electrode polarization, ie., build-up of charge on the electrodes.

For each defibrillator method discussed above, the initial first phase voltage A may be the same for all patients or it may be selected automatically or by the defibrillator user. For example, the defibrillator may have a selection of initial voltage settings, one for an infant, a second for an adult, and a third for use in open heart surgery. In addition, the defibrillator may deliver a waveform that has a minimum voltage or current at the beginning and/or at the end of a waveform phase.

Figure 10:
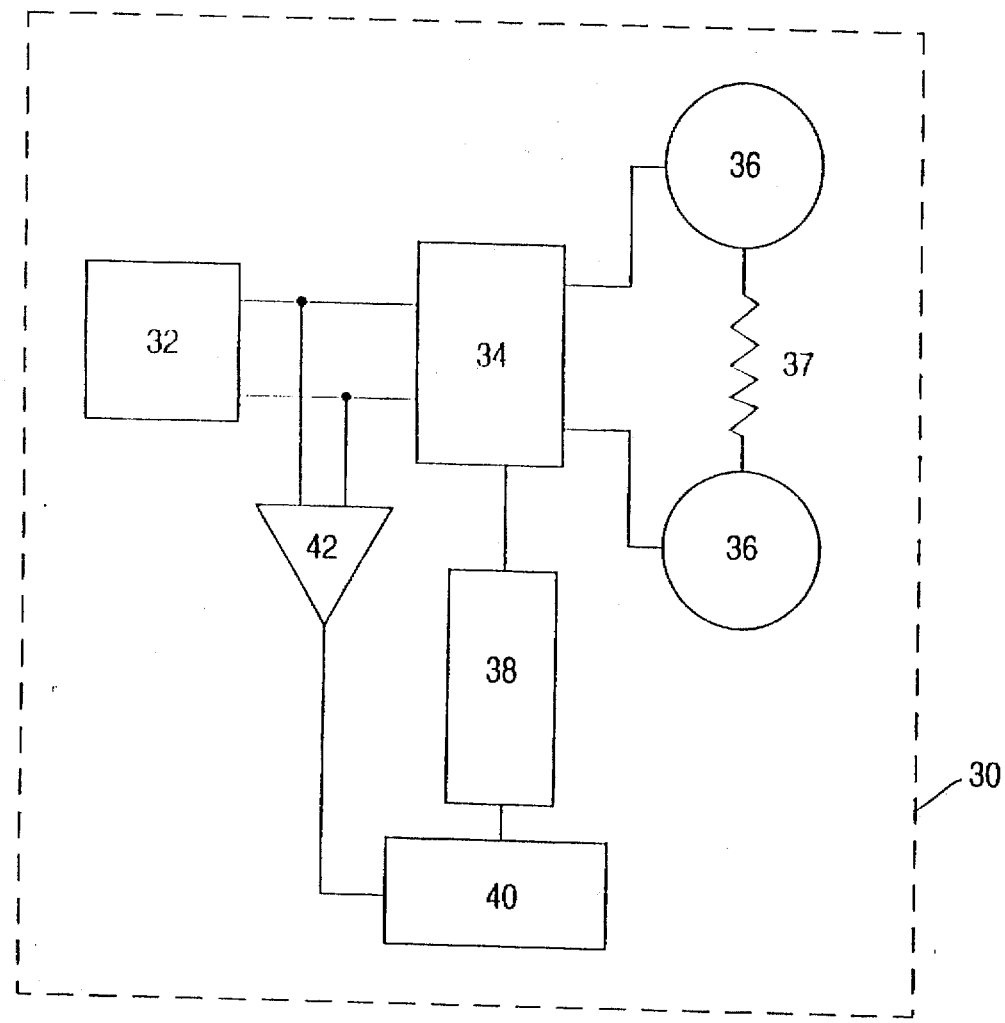
FIG. 10 is a block diagram of a defibrillator system according to a preferred embodiment of this invention.

FIG. 10 is a schematic block diagram of a defibrillator system according to a preferred embodiment of this invention. The defibrillator system 30 comprises an energy source 32 to provide the voltage or current pulses described above. In one preferred embodiment, energy source 32 is a single capacitor or a capacitor bank arranged to act as a single capacitor. A connecting mechanism 34 selectively connects and disconnects energy source 32 to and from a pair of electrodes 36 electrically attached to a patient, represented here as a resistive load 37. The connections between the electrodes and the energy source may be in either of two polarities with respect to positive and negative terminals on the energy source.

The defibrillator system is controlled by a controller 38. Specifically, controller 38 operates the connecting mechanism 34 to connect energy source 32 with electrodes 36 in one of the two polarities or to disconnect energy source 32 from electrodes 36. Controller 38 receives timing information from a timer 40, and timer 40 receives electrical information from electrical sensor 42 connected across energy source 32. In some preferred embodiments, sensor 42 is a voltage sensor; in other preferred embodiments, sensor 42 is a current sensor.

Figure 11:
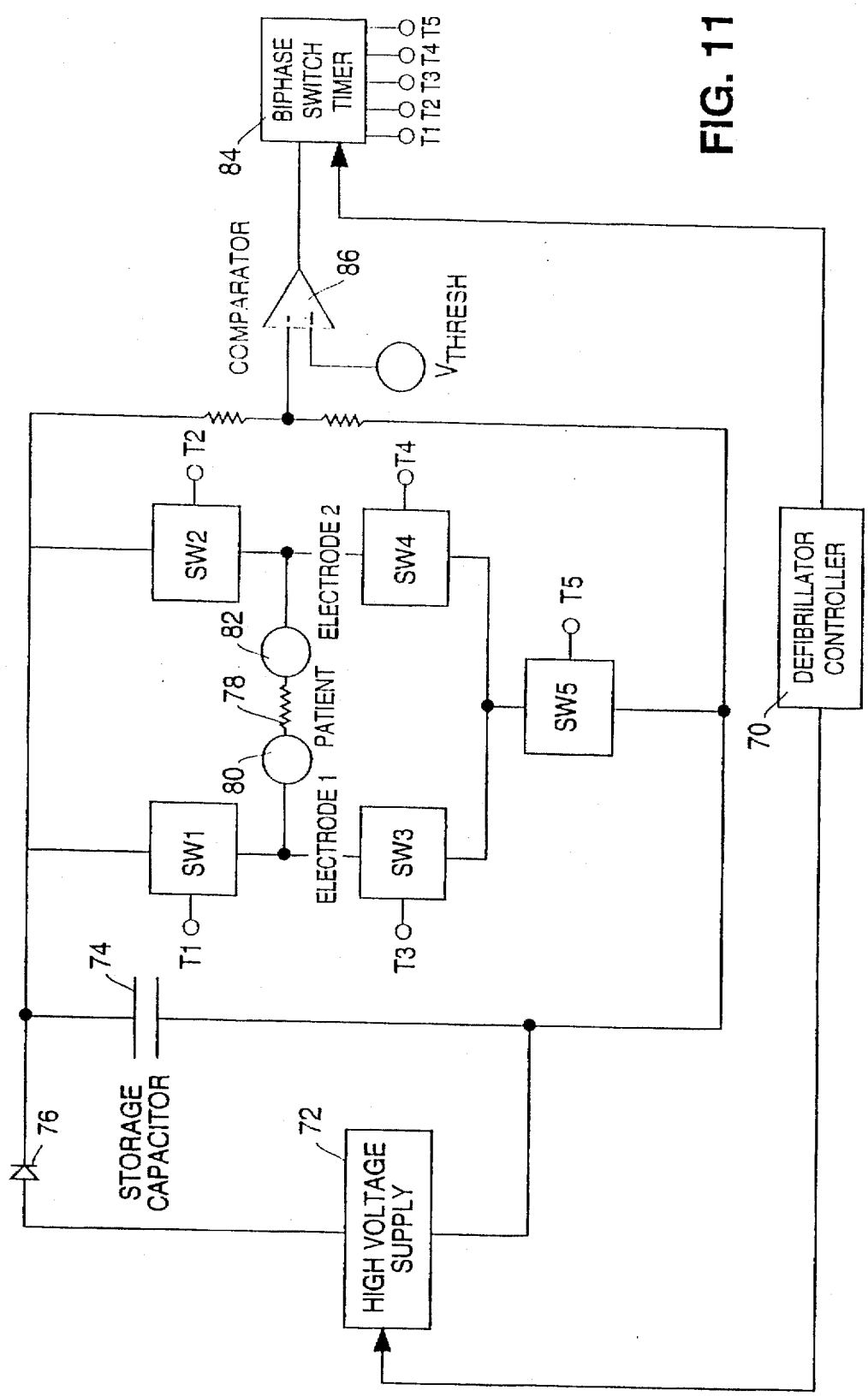
FIG. 11 is a schematic circuit diagram of a defibrillator system according to a preferred embodiment of this invention.

FIG. 11 is a schematic circuit diagram illustrating a device according to the preferred embodiments discussed above. Defibrillator controller 70 activates a high voltage power supply 72 to charge storage capacitor 74 via diode 76 to a predetermined voltage. During this period, switches SW1, SW2, SW3 and SW4 are turned off so that no voltage is applied to the patient (represented here as resistor 78) connected between electrodes 80 and 82. SW5 is turned on during this time.

After charging the capacitor, controller 70 de-activates supply 72 and activates biphase switch timer 84. Timer 84 initiates discharge of the first phase of the biphasic waveform through the patient in a first polarity by simultaneously turning on switches SW1 and SW4 via control signals T1 and T4, while switch SW5 remains on to deliver the initial voltage A through electrodes 80 and 82 to the patient 78.

Depending on the operating mode, delivery of the first phase of the biphasic pulse may be terminated by the timer 84 after the end of a predetermined period or when the voltage across the electrodes has dropped below a predetermined value as measured by comparator 86. Timer 84 terminates pulse delivery by turning off switch SW5 via control signal T5, followed by turning off switches SW1 and SW4. The voltage across electrodes 80 and 82 then returns to zero.

During the interim period G, SW5 is turned on to prepare for the second phase. After the end of interim period G, timer 84 initiates delivery of the second phase by simultaneously turning on switches SW2 and SW3 via control signals T2 and T3 while switch SW5 remains on. This configuration applies voltage from the capacitor to the electrodes at an initial second phase voltage C and in a polarity opposite to the first polarity. Timer 84 terminates delivery of the second phase by turning off switch SW5 via control signal T5, followed by turning off switches SW2 and SW3. The second phase may be terminated at the end of a predetermined period or when the voltage measured by comparator 86 drops below a second phase termination voltage threshold.

In a preferred embodiment, switch SW5 is an insulated gate bipolar transistor (IGBT) and switches SW1–SW4 are silicon-controlled rectifiers (SCRs). The SCRs are avalanche-type switches which can be turned on to a conductive state by the application of a control signal, but cannot be turned off until the current through the switch falls to zero or near zero. Thus, the five switches can be configured so that any of the switches SW1–SW4 will close when SW5 is closed and will reopen only upon application of a specific control signal to SW5.

This design has the further advantage that switch SW5 does not need to withstand the maximum capacitor voltage. The maximum voltage that will be applied across switch SW5 will occur when the first phase is terminated by turning SW5 off, at which time the capacitor voltage has decayed to some fraction of its initial value.

Other switches and switch configurations may be used, of course without departing from the scope of the invention. In addition, the defibrillator configurations of FIGS. 10 and 11 may be used to deliver electric pulses of any polarity, amplitude, and duration singly and in any combination.

Figure 12:
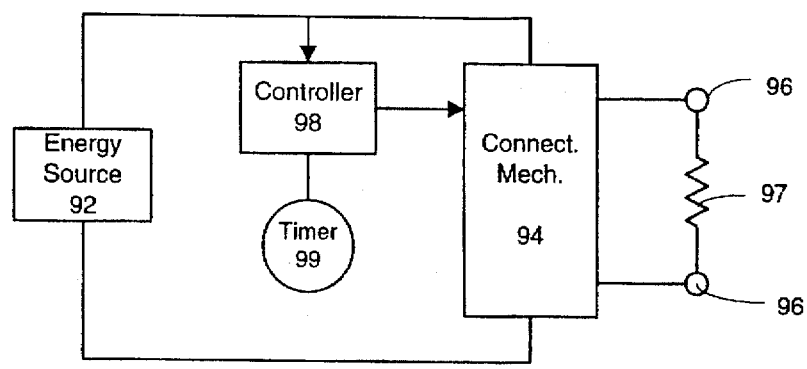
FIG. 12 is a block diagram showing another embodiment of the external defibrillator system of this invention.

FIG. 12 is a block diagram showing another embodiment of the defibrillator system of this invention. The defibrillator system 90 comprises an energy source 92 to provide a voltage or current pulse. In one preferred embodiment, energy source 92 is a single capacitor or a capacitor bank arranged to act as a single capacitor.

A connecting mechanism 94 selectively connects and disconnects a pair of electrodes 96 electrically attached to a patient (represented here as a resistive load 97) to and from the energy source. The connections between the electrodes and the energy source may be in either of two polarities with respect to positive and negative terminals on the energy source.

The defibrillator system is controlled by a controller 98. Specifically, controller 98 operates the connecting mechanism 94 to connect energy source 92 with electrodes 96 in one of the two polarities or to disconnect energy source 92 from electrodes 96. Controller 98 receives discharge information (such as current, charge and/or voltage) from the discharge circuit. Controller 98 may also receive timing information from a timer 99.

Controller 98 uses information from the discharge circuit and/or the timer to control the shape of the waveform delivered to the patient in real time (i.e., during delivery of the waveform), such as by selecting appropriate waveform parameters from a memory location associated with the controller or by otherwise adjusting the duration of the phases of the biphasic waveform. By controlling the waveform shape, the system controls the duration, tilt and total delivered energy of the waveform. For example, biphasic waveforms with relatively longer first phases have better conversion properties than waveforms with equal or shorter first phases, provided the total duration exceeds a critical minimum. Therefore, in the case of high impedance patients, it may be desirable to increase the duration of the first phase of the biphasic waveform relative to the duration of the second phase to increase the overall efficacy of the electrotherapy by delivering a more efficacious waveform and to increase the total amount of energy delivered.

Figure 13:
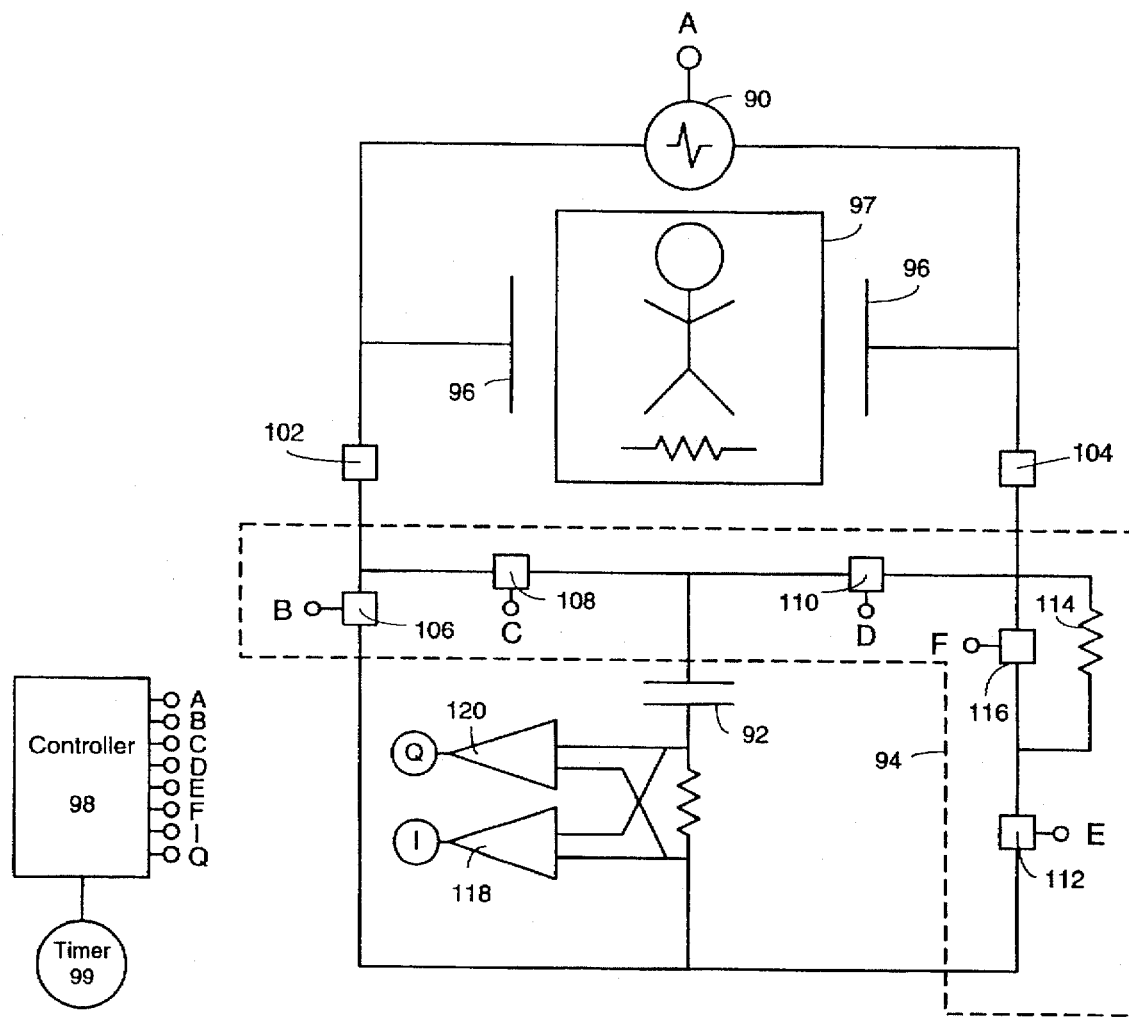
FIG. 13 is a schematic diagram of a defibrillator system according to a preferred embodiment of this invention.

A preferred embodiment of a defibrillator system according to the invention is shown schematically in FIG. 13. In this diagram, the energy source is a capacitor 92 preferably having a size between 60 and 150 microfarads, most preferably 100 microfarads. The system also includes a charging mechanism (not shown) for charging the capacitor to an initial voltage.

A controller 98 controls the operation of the defibrillator to deliver a shock to the patient 97 through electrodes 96 automatically in response to a detected arrhythmia or manually in response to a human operator. FIG. 13 shows an ECG system 100 attached to the electrodes to provide ECG monitoring and/or arrhythmia detection. FIG. 13 also shows a pair of switches 102 and 104 isolating the patient and the ECG system from the defibrillation circuitry. Switches 102 and 104 may be any suitable kind of isolators, such as mechanical relays, solid state devices, spark gaps, or other gas discharge devices. The ECG system and the isolation switches are not essential parts of this invention.

In this embodiment, the connecting mechanism 94 includes four switches 106, 108, 110 and 112 operated by the controller 98 to deliver a shock from the energy source 92 to the patient. The preferred embodiment also may include an optional current limiting circuit comprising a resistor 114 and switch 116 to provide additional protection to the defibrillator circuit components and to the defibrillator operator. The operation of the isolation switches and the connecting mechanism to deliver a waveform to the patient is described below.

For purposes of this description, it is assumed that all switches are open prior to discharge. It should be understood that this need not be the case. For example, switches 106, 112 and 116 could start out in the closed position, with the operating sequence of the switches modified accordingly.

In response to a request for a shock, the controller first closes switches 102 and 104, then switch 112, then switch 108 to initiate delivery of a limited shock to the patient. A current sensor 118 monitors the current delivered by the capacitor. If the peak current is below a circuit safety threshold, then switch 116 is closed to take safety resistor 114 out of the circuit. Peak current values above the threshold could indicate a short circuit condition.

In the preferred embodiment, the duration of the first and second phases of the biphasic waveform are determined by measuring a patient-dependent electrical parameter. As described in more detail below, the measured parameter in the preferred embodiment is the time it takes for a predetermined amount of charge to be delivered by the energy source to the patient. Charge control can provide better noise immunity than other waveform monitoring methods, such as voltage or current monitoring.

The system shown in FIG. 13 uses a current integrator 120 to provide charge information to the controller. The controller sets the duration of the first and second waveform phases (thereby controlling the waveform shape) based on charge information from current integrator 120. Other means of determining phase durations may be used, of course, without departing from the scope of the invention.

At the end of the first phase of the waveform, the controller opens switch 112 to terminate delivery of the shock. Switch 116 may also be opened at any time from this point on. The controller opens switch 108 as well.

After the lapse of a brief interphase period, the controller closes switches 106 and 110 to initiate delivery of the second phase of the waveform. In the preferred embodiment the second phase duration is determined by the first phase duration. Other means of determining second phase duration are within the scope of the invention, however. At the end of the second phase, the controller opens switch 106 to terminate delivery of the shock. Switches 110, 102 and 104 are opened thereafter.

The following example illustrates a specific implementation of the method and apparatus of this invention. The invention is not limited to the values and circuit elements discussed in this example.

In this example, switches 102 and 104 are implemented as a double pole, double throw mechanical relay. Switches 108 and 110 are each implemented as a pair of SCR's in series in order to meet required standoff voltages with currently available components. Switch 106 is implemented as two insulated gate bipolar transistors ("IGBT's") in series, again due to high voltage requirements.

The functions of switches 116 and 112 are shared among three IGBT's to meet voltage standoff requirements, with one IGBT being on at the same time as switch 116 and off at the same time as switch 112. In this implementation resistor 114 is split into two resistors to equally divide the voltage across the IGBT's.

The current sensor 118 may be used to send current information to the controller for purposes of, e.g., short circuit protection, leads off detection, etc. The manner in which the short circuit or leads off conditions are detected are beyond the scope of this invention. The integrator 120 and current sensor 118 may each be an op-amp feeding a threshold comparator for detecting charge and current limits, respectively. The integrator could be provided with a switch for resetting to initial conditions prior to a waveform delivery.

A comparator associated with the current integrator monitors the charge delivered to the patient and sends a signal to the waveform controller when the charge reaches 0.06182 Coulombs (referred to as "Qt"). The time required to reach that charge ("t(Qt)") is monitored by the controller using an up/down counter which counts a scaled down reference frequency. One element of the frequency scaler is a selectable 2:3 pre-scaler. The pre-scaler is set to 3 during the first phase. In this example, eleven time thresholds are stored in the controller, which determines the first phase duration ("t($\phi$1)") based on the time required to reach Qt. At each time threshold, a new value of t($\phi$1) is loaded until Qt is reached. If Qt is not reached within 6.35 mS, then t($\phi$1) is set to 12 mS. The counter runs at the scaled down frequency during delivery of the entire first phase.

Some exemplary values for Qt thresholds and t($\phi$1) are shown in Table I.

TABLE I

| If t(Qt) < (mS) | Then t($\phi$1) is (mS) |
|---|---|
| 1.13 | 2.3 |
| 1.60 | 2.85 |
| 2.07 | 3.79 |
| 2.56 | 4.02 |
| 3.07 | 4.83 |
| 3.58 | 6.76 |
| 4.10 | 7.73 |
| 4.64 | 8.69 |
| 5.20 | 9.66 |
| 5.77 | 10.62 |
| 6.35 | 11.59 |

In this example, the interphase delay is set at 300 82 S. At 0 µS the first phase IGBT's are opened, terminating the first phase. At 250 µS, the second phase IGBT's are closed. At 300 µS the second phase SCR's are closed, initiating the second phase.

In this example, second phase timing is determined by first phase timing. Specifically, the count value accumulated during phase one (2.3 mS to 12 mS) is used to control the duration of the second phase. During the second phase, the counter that had been counted up during the first phase is counted down to 0, at which time the second phase is terminated. The actual duration of the second phase depends on the scaled down frequency used to run down the counter. If the first phase t(Qt) was less than 3.07 mS, then the reference clock prescaler is set to 3 to a give second phase duration equal to the first phase duration. If t(Qt) is greater than or equal to 3.07 mS, then the pre-scaler is set to 2, giving a second phase duration which is ⅔ of the first phase duration.

In an alternative embodiment, the measured patient-dependent electrical parameter is capacitor voltage. A comparator monitors the capacitor voltage and sends a signal to the waveform controller when the voltage decays to 1000 volts (Vt). As in the charge control embodiment, the time required to reach that voltage is monitored by the controller using an up/down counter which counts a scaled down reference frequency. The first phase duration (t($\phi$1)) is based on the time required to reach Vt. The method of selecting the appropriate t($\phi$1) is identical to the charge control embodiment. If Vt is not reached within 6.18 mS, then t($\phi$1) is set to 12 mS. Table II shows the t(Vt) thresholds and their associated t($\phi$1).

TABLE II

| If t(Vt) < (mS) | Then t($\phi$1) is (mS) |
|---|---|
| 1.24 | 2.3 |
| 1.73 | 2.85 |
| 2.23 | 3.79 |
| 2.72 | 4.02 |
| 3.22 | 4.83 |
| 3.71 | 6.76 |
| 4.20 | 7.73 |
| 4.70 | 8.69 |
| 5.19 | 9.66 |
| 5.69 | 10.62 |
| 6.18 | 11.59 |

Interphase delay and second phase timing is identical to the charge control method.

Figure 14:
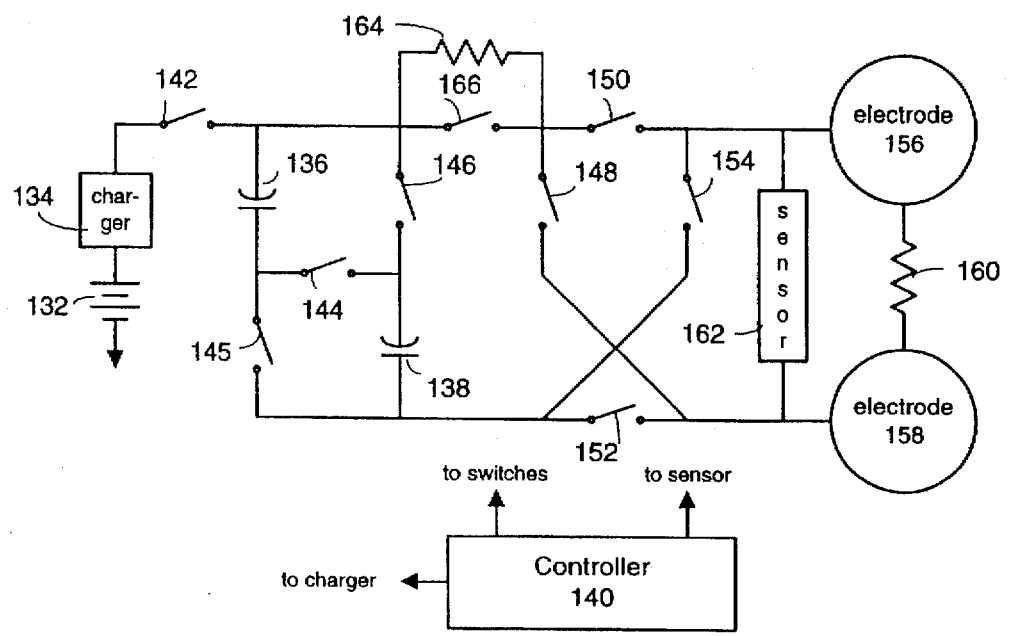
FIG. 14 is a schematic diagram of yet another embodiment of this invention.

Yet another embodiment of the invention is shown in FIG. 14. The energy source for the external defibrillator 130 of FIG. 14 is a battery 132 providing power (via a charging device 134) to two capacitors 136 and 138 under the control of controller 140. Controller 140 also controls switches 144–154 to deliver energy from capacitors 136 and/or 138 to a patient (represented in FIG. 14 by resistor 160) through electrodes 156 and 158.

The embodiment of FIG. 14 may also include a safety resistor 164 and a safety resistor switch 166 to limit the current delivered by the capacitor(s) until it can be determined whether a short circuit condition exists, as discussed above.

Figure 15:
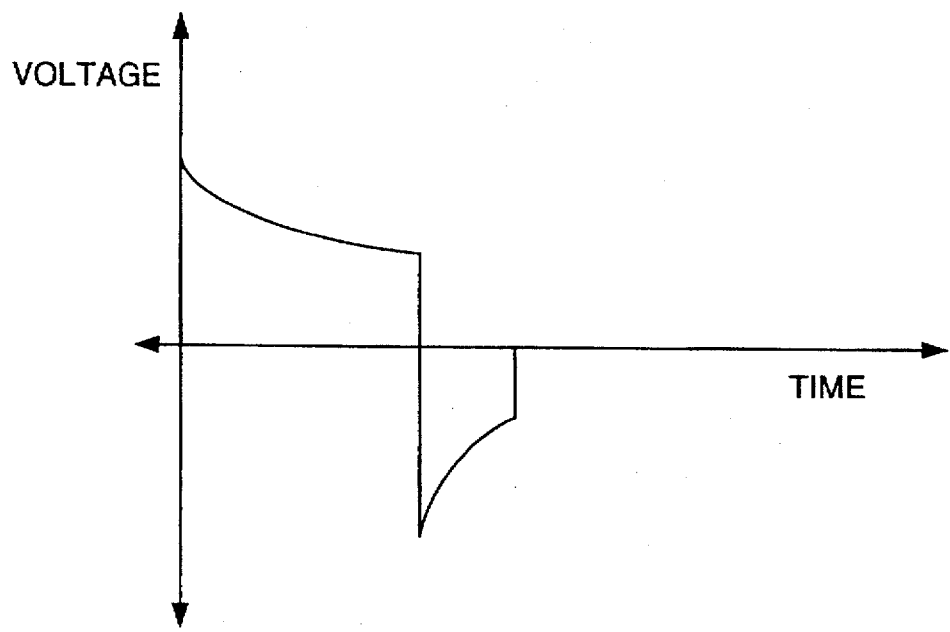
FIG. 15 is a schematic representation of a biphasic waveform delivered by the external defibrillator shown in FIG. 14.

A sensor 162, which is preferably either a current sensor or a voltage sensor, monitors a patient-dependent electrical parameter and sends information regarding the monitored parameter to controller 140. The arrangement of the capacitors and switches in the embodiment of FIG. 14 permits the defibrillator to modify the parameters of the delivered waveform to compensate for patient-to-patient impedance differences, as monitored by sensor 162. For example, if the patient's impedance is high (e.g., over 125 Ω), the defibrillator could deliver a truncated exponential biphasic waveform as follows: (1) Deliver the first phase with switches 145, 146, 166 (assuming the device has determined there is no short circuit), 150 and 152 closed and switches 144, 148, 154 open. Capacitors 136 and 138 are thus connected in parallel. (2) Monitor a patient-dependent electrical parameter (such as voltage, current or charge) via sensor 162 during at least a portion of the first phase. (3) If the patient-dependent electrical parameter indicates that the electrodes are connected to a high-impedance patient, deliver the second phase of the waveform with switches 145, 146, 150 and 152 open and switches 144, 166, 148 and 154 closed to connect capacitors 136 and 138 in series and to reverse the polarity of the waveform delivery. The resulting waveform has a shape similar to that shown in FIG. 15. Note that the leading edge of the second phase of the waveform has a higher voltage than the trailing edge of the first phase.

As another example, if the patient's impedance is low, as detected, e.g., by sensor 162, the defibrillator could deliver a truncated exponential biphasic waveform using only capacitor 136 by keeping switches 144 and 146 open from the start of waveform delivery (if the patient's impedance is known before waveform delivery begins) or by opening switches 144 and 146 shortly after waveform delivery begins to remove capacitor 136 from the circuit.

Alternatively, if the patient's impedance is high, the defibrillator could deliver a waveform with capacitors 136 and 138 arranged in series from the start of waveform delivery (if the patient's impedance is known before waveform delivery begins) or by opening switches 145 and 146 and closing switch 144 shortly after waveform delivery begins.

As an alternative to measuring a patient-dependent electrical parameter and configuring the capacitors during delivery of the waveform, the defibrillator could use information regarding patient impedance gathered prior to waveform delivery (such as during a prior waveform delivery) to determine the position of the switches and the configuration of the capacitors.

It should also be noted that while the embodiment of FIG. 14 uses two capacitors, any number of capacitors greater than one could be used without departing from the scope of the invention.

Figure 16:
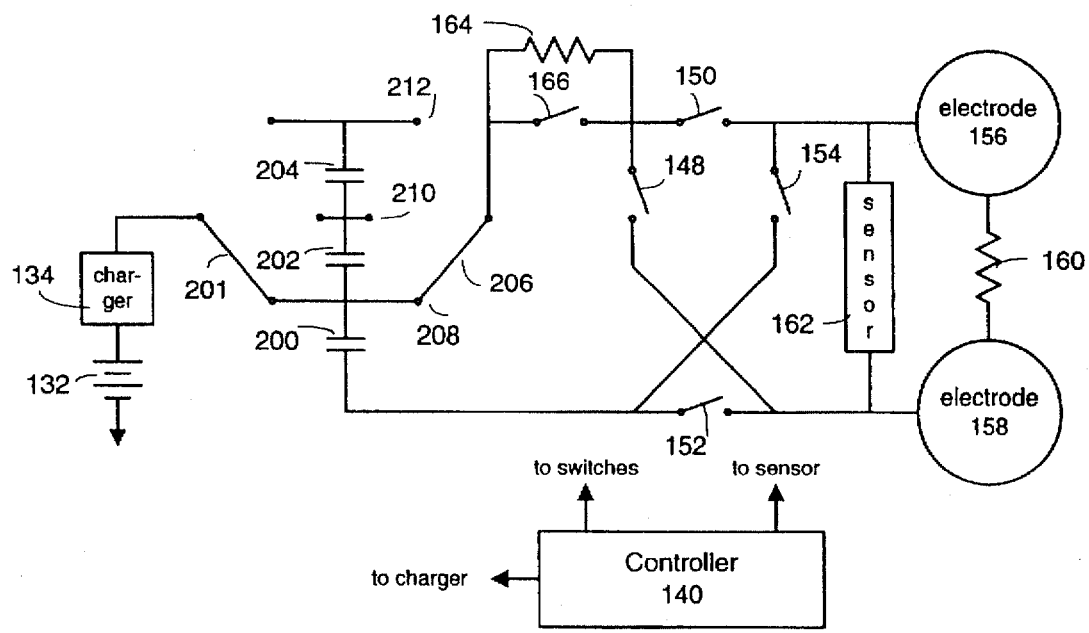
FIG. 16 is a schematic diagram of another embodiment of this invention.

FIG. 16 is a schematic drawing of another embodiment of this invention. (Elements common with the FIG. 14 embodiment have been given the same element numbers.) In this embodiment, three capacitors 208, 210, and 212 are connectable in series via a three-way switch 206. In the position shown in FIG. 16 (i.e., at switch position 208), only capacitor 200 is connected to the external defibrillator waveform delivery circuit. If switch 206 is at switch position 210, capacitors 200 and 202 are connected to the waveform delivery circuit in series. Finally, if switch 206 is at switch position 212, all three capacitors are connected to the waveform delivery circuit in series.

Likewise, an optional three-way switch 201 can be positioned to charge only capacitor 200 (when configured as shown), capacitors 200 and 202 together, or all capacitors together. Alternatively, all capacitors could be charged together each time, even if fewer than all capacitors will be discharged to treat a patient.

As in the FIG. 14 embodiment, the capacitors in FIG. 16 can be configured to provide an optimal voltage or current (and thereby optimal energy) to the patient. For example, high impedance patients will benefit from a series connection of all three capacitors, while low impedance patients may require only one or two capacitors. As in the FIG. 14 embodiment, the capacitors may be arranged during delivery of the waveform based on a value of a patient-dependent electrical parameter (such as voltage, current or charge) as monitored by sensor 162, e.g., by adjusting the initial voltage or current of a phase of a multiphasic waveform. Alternatively, the external defibrillator could use information regarding patient impedance gathered prior to waveform delivery (such as during a prior waveform delivery) to determine the position of the switch 206 and the configuration of the capacitors. It should be understood that any number of capacitors may be used in the serial capacitor arrangement of FIG. 16. The greater the number of capacitors, the more likely the waveform delivered by the external defibrillator will be titrated to be most efficacious for a particular patient.

Figure 17:
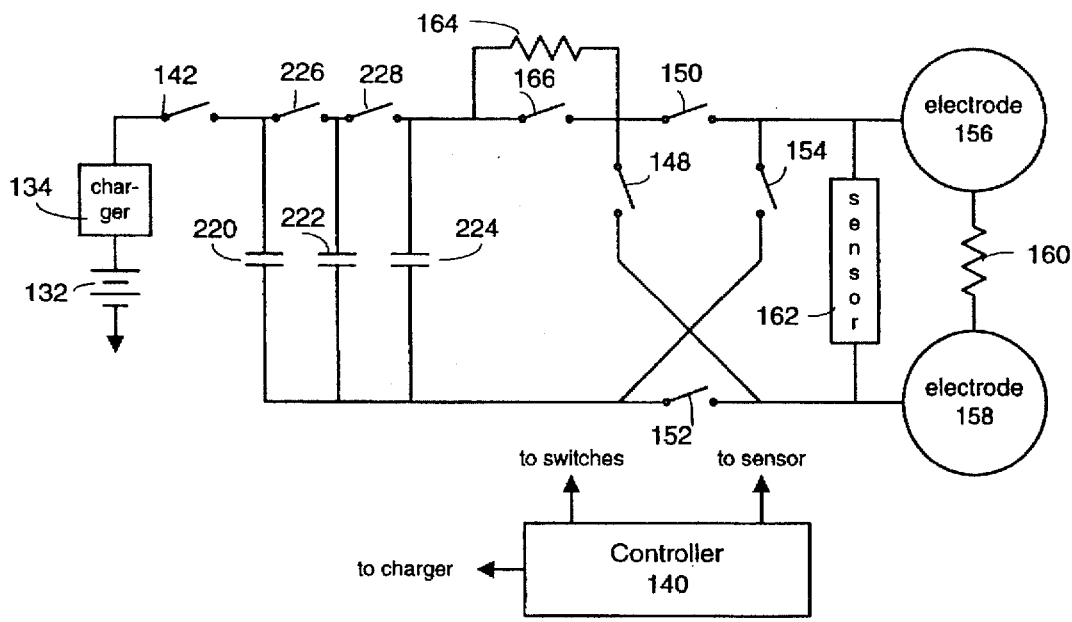
FIG. 17 is a schematic diagram of yet another embodiment of this invention.

Yet another embodiment of the invention is shown in FIG. 17. In this embodiment, three capacitors 220, 222 and 224 are arranged in parallel. With switches 228 and 226 in the open position as shown in FIG. 17, only capacitor 224 will provide energy to the external defibrillator waveform delivery circuit. If additional energy is needed, switch 228 could be closed by controller 140 to add capacitor 222 to the circuit. If even more energy is needed, switch 226 could be closed by controller 140 to place all three capacitors in a parallel arrangement within the waveform delivery circuit. The positions of the switches and the arrangement of the capacitors can be adjusted during waveform delivery, based on a value of a patient-dependent electrical parameter monitored by sensor 162. Alternatively, the optimal switch positions (and therefore optimal energy delivery and/or waveform phase durations) can be determined prior to delivery of the waveform.

Other arrangements and operating algorithms will be apparent to those skilled in the art. In addition, while the invention has been discussed with reference to external defibrillators, one or more aspects of the invention would be applicable to implantable defibrillators as well.

What is claimed is:

1. A method for delivering electrotherapy to a patient through electrodes connectable to a plurality of capacitors, the method comprising the following steps:

discharging at least one of the capacitors across the electrodes to deliver electrical energy to the patient;

monitoring a patient-dependent electrical parameter during the discharging step; and adjusting energy delivered to the patient based on a value of the electrical parameter.

2. The method of claim 1 wherein the electrical parameter is voltage.

3. The method of claim 1 wherein the electrical parameter is current.

4. The method of claim 1 wherein the electrical parameter is charge.

5. The method of claim 1 wherein the discharging step comprises discharging the plurality of capacitors across the electrodes to deliver energy to the patient in a waveform having more than one phase.

6. The method of claim 5 wherein the adjusting step comprises selecting a serial or a parallel arrangement for the capacitors based on a value of the electrical parameter to deliver energy to the patient.

7. A method for delivering electrotherapy to a patient through electrodes connectable to a plurality of capacitors, the method comprising the following steps:

discharging at least one of the capacitors across the electrodes to deliver electrical energy to the patient in a multiphasic waveform;

monitoring a patient-dependent electrical parameter during the discharging step; and shaping the waveform so that an initial parameter of a waveform phase depends on a value of the electrical parameter.

8. The method of claim 7 wherein the shaping step comprises shaping the waveform so that an initial parameter of a later phase of the multiphasic waveform has a greater value than an initial value of an earlier phase of the multiphasic waveform depending on a value of the electrical parameter.

9. The method of claim 7 wherein the electrical parameter is voltage.

10. The method of claim 7 wherein the electrical parameter is current.

11. The method of claim 7 wherein the electrical parameter is charge.

12. The method of claim 7 wherein the shaping step comprises selecting a serial or a parallel arrangement for the capacitors based on a value of the electrical parameter to deliver energy to the patient.

13. The method of claim 7 wherein the adjusting step comprises selecting a serial or a parallel arrangement for the capacitors based on a value of the electrical parameter to deliver energy to the patient.

14. The method of claim 7 wherein the adjusting step comprises using fewer than all of the capacitors to deliver energy to the patient.

15. A method for delivering electrotherapy to a patient through electrodes connected to an energy source, the method comprising the following steps:

discharging the energy source across the electrodes to deliver electrical energy to the patient in a multiphasic truncated exponential waveform;

monitoring current delivered by the energy source to the patient during the discharging step; and controlling waveform delivery based on the current delivered so that the waveform has at least one of a minimum phase start current or a minimum phase end current.

16. The method of claim 15 wherein the controlling step comprises controlling waveform delivery based on the current delivered so that the waveform has at least a minimum phase end current.

17. The method of claim 15 wherein the controlling step comprises controlling waveform delivery based on the current delivered so that the waveform has at least a minimum phase start current.

* * * * *

UNITED STATES PATENT AND TRADEMARK OFFICE
CERTIFICATE OF CORRECTION

PATENT NO. : 5,749,904
DATED : May 12, 1998
INVENTOR(S) : Gliner et al.

It is certified that error appears in the above-identified patent and that said Letters Patent is hereby corrected as shown below:

Column 1, (line 58), delete "patients" and insert therefor --patient's--.

Column 5, (line 19), after "choices.", start a new paragraph.

Column 6, (line 43), delete "$V_{THRESH}$" and insert therefor --$t_{THRESH}$--.

Column 7, (line 25), delete "$T_{THRESH}$" and insert therefor --$t_{THRESH}$--.

Column 11, (line 40), delete "300 82 S" and insert therefor --300 $\mu$S--.

Column 13, (line 51), after "capacitors.", start a new paragraph.

Signed and Sealed this

Sixteenth Day of March, 1999

Attest:

Q. TODD DICKINSON

Attesting Officer

Acting Commissioner of Patents and Trademarks